United States Patent [19]

Kiefer

[11] Patent Number: 5,385,893

[45] Date of Patent: Jan. 31, 1995

[54] TRICYCLOPOLYAZAMACROCYCLOPHOS-PHONIC ACIDS, COMPLEXES AND DERIVATIVES THEREOF, FOR USE AS CONTRAST AGENTS

[75] Inventor: Garry E. Kiefer, Lake Jackson, Tex.

[73] Assignee: The Dow Chemical Company, Midland, Mich.

[21] Appl. No.: 58,622

[22] Filed: May 6, 1993

[51] Int. Cl.$^6$ .................. A61K 31/44; A61K 31/675; C07D 471/18; C07D 471/22

[52] U.S. Cl. ........................ 514/80; 514/286; 514/293; 424/9; 530/386; 530/387.1; 540/465; 540/472

[58] Field of Search ............... 540/465, 472; 514/80, 514/286, 293; 424/9

[56] References Cited

U.S. PATENT DOCUMENTS

| | | | |
|---|---|---|---|
| 2,609,390 | 6/1950 | Bernsworth | 260/500 |
| 3,331,773 | 7/1967 | Gunderson | 210/58 |
| 3,336,221 | 7/1967 | Ralston | 219/58 |
| 3,434,969 | 3/1969 | Ralston | 210/58 |
| 4,880,008 | 11/1989 | Lauffer | 128/654 |
| 4,899,755 | 2/1990 | Lauffer | 128/654 |
| 4,980,148 | 12/1990 | Dean | 424/9 |

OTHER PUBLICATIONS

J. Org. Chem., 53, 3521–3529 (1988), Bottino et al.
J. Nucl Med., 25, 506–513 (1984), Koutcher et al.
C. J. Broan et al., J. Chem. Soc., Chem. Commun., 1739–1741 (1990).
C. J. Broan et al., J. Chem. Soc., Chem Commun., 1738–1739 (1990).
I. K. Adzamli et al., J. Med Chem., 32, 139, 144 (1989).
J. Magnetic Resonance, 33, 83–106 (1979), Brunner et al.
Magnetic Resonance Annual, 231–266 Raven Press, N.Y. (1985), Wolf et al.
Frontiers of Biol. Energetics 1, 752–759 (1978), Lauterbur et al.

*Primary Examiner*—Mukund J. Shah
*Assistant Examiner*—P. I. Datlow
*Attorney, Agent, or Firm*—Karen L. Kimble

[57] ABSTRACT

Tri- and tetra-cyclopolyazamacrocyclophosphonic acid compounds and their derivatives are disclosed which may form inert complexes with Gd, Mn or Fe ions. The overall charge of the complex can be varied to alter the in vivo biolocalization. The complexes are useful as contrast agents for diagnostic purposes.

27 Claims, No Drawings

TRICYCLOPOLYAZAMACROCYCLOPHOS-PHONIC ACIDS, COMPLEXES AND DERIVATIVES THEREOF, FOR USE AS CONTRAST AGENTS

This invention concerns ligands that are tricyclopolyazamacrocyclophosphonic acids, complexes and derivatives thereof, for use as contrast agents in magnetic resonance imaging (MRI). To better understand this invention, a brief background on MRI is provided in the following section.

BACKGROUND OF THE INVENTION

MRI is a non-invasive diagnostic technique which produces well resolved cross-sectional images of soft tissue within an animal body, preferably a human body. This technique is based upon the property of certain atomic nuclei (e.g. water protons) which possess a magnetic moment [as defined by mathematical equations: see G. M. Barrow, *Physical Chemistry*, 3rd Ed., McGraw-Hill, N.Y. (1973)] to align in an applied magnetic field. Once aligned, this equilibrium state can be perturbed by applying an external radio frequency (RF) pulse which causes the protons to be tilted out of alignment with the magnetic field. When the RF pulse is terminated, the nuclei return to their equilibrium state and the time required for this to occur is known as the relaxation time. The relaxation time consists of two parameters known as spin-lattice (T1) and spin-spin (T2) relaxation and it is these relaxation measurements which give information on the degree of molecular organization and interaction of protons with the surrounding environment.

Since the water content of living tissue is substantial and variations in content and environment exist among tissue types, diagnostic images of biological organisms are obtained which reflect proton density and relaxation times. The greater the differences in relaxation times (T1 and T2) of protons present in tissue being examined, the greater will be the contrast in the obtained image [*J. Magnetic Resonance* 33, 83–106 (1979)].

It is known that paramagnetic chelates possessing a symmetric electronic ground state can dramatically affect the T1 and T2 relaxation rates of juxtaposed water protons and that the effectiveness of the chelate in this regard is related, in part, to the number of unpaired electrons producing the magnetic moment [*Magnetic Resonance Annual*, 231–266, Raven Press, N.Y. (1985)]. It has also been shown that when a paramagnetic chelate of this type is administered to a living animal, its effect on the T1 and T2 of various tissues can be directly observed in the magnetic resonance (MR) images with increased contrast being observed in the areas of chelate localization. It has therefore been proposed that stable, non-toxic paramagnetic chelates be administered to animals in order to increase the diagnostic information obtained by MRI [*Frontiers of Biol. Energetics I*, 752–759 (1978); *J. Nucl. Med.* 25, 506–513 (1984); *Proc. of NMR Imaging Symp.* (Oct. 26–27, 1980); F. A. Cotton et al., *Adv. Inorg. Chem.* 634–639 (1966)]. Paramagnetic metal chelates used in this manner are referred to as contrast enhancement agents or contrast agents.

There are a number of paramagnetic metal ions which can be considered when undertaking the design of an MRI contrast agent. In practice, however, the most useful paramagnetic metal ions are gadolinium ($Gd^{+3}$), iron ($Fe^{+3}$), manganese ($Mn^{+2}$) and ($Mn^{+3}$), and chromium ($Cr^{+3}$), because these ions exert the greatest effect on water protons by virtue of their large magnetic moments. In a non-complexed form (e.g. $GdCl_3$), these metal ions are toxic to an animal, thereby precluding their use in the simple salt form. Therefore, a fundamental role of the organic chelating agent (also referred to as a ligand) is to render the paramagnetic metal non-toxic to the animal while preserving its desirable influence on T1 and T2 relaxation rates of the surrounding water protons.

Art in the MRI field is quite extensive, such that the following summary, not intended to be exhaustive, is provided only as a review of this area and other compounds that are possibly similar in structure. U.S. Pat. No. 4,899,755 discloses a method of alternating the proton NMR relaxation times in the liver or bile duct of an animal using $Fe^{+3}$-ethylene-bis(2-hydroxyphenylglycine) complexes and its derivatives, and suggests among various other compounds the possible use of a pyridine macrocyclomethylenecarboxylic acid. U.S. Pat. No. 4,880,008 (a CIP of U.S. Pat. No. 4,899,755) discloses additional imaging data for liver tissue of rats, but without any additional complexes being shown. U.S. Pat. No. 4,980,148 disclose gadolinium complexes for MRI which are non-cyclic compounds. C. J. Broan et al., *J. Chem. Soc., Chem. Commun.*, 1739–1741 (1990) describe some bifunctional macrocyclic phosphinic acid compounds. C. J. Broan et al., *J. Chem. Soc., Chem. Commun.*, 1738–1739 (1990) describe compounds that are triazabycyclo compounds. I. K. Adzamli et al., *J. Med. Chem.* 32, 139–144 (1989) describes acyclic phosphonate derivatives of gadolinium complexes for NMR imaging.

At the present time, the only commercial contrast agents available in the U.S. are the complex of gadolinium with diethylenetriaminepentaacetic acid (DTPA-$Gd^{+3}$- Magnevist TM by Shering) and a DO3A derivative [1,4,7-tris(carboxymethyl)-10-(2-hydroxypropyl)-1,4,7,10-tetraazacyclododecanato]-gadolinium (Prohance TM by Squibb). Magnevist TM and Prohance TM are considered as non-specific/perfusion agents since they freely distribute in extracellular fluid followed by efficient elimination through the renal system. Magnevist TM has proven to be extremely valuable in the diagnosis of brain lesions since the accompanying breakdown of the blood/brain barrier allows perfusion of the contrast agent into the affected regions. In addition to Magnevist TM, Guerbet is commercially marketing a macrocyclic perfusion agent [1,4,7,10-tetrakis(carboxymethyl)-1,4,7,10-tetraazacyclododecanato]-gadolinium (Dotarem TM) which presently is only available in Europe. Prohance TM is shown to have fewer side effects than Magnevist TM. A number of other potential contrast agents are in various stages of development.

SUMMARY OF THE INVENTION

The present invention is directed to novel ligands that are tri- and tetra-cyclopolyazamacrocyclic compounds, and derivatives thereof, of the formula

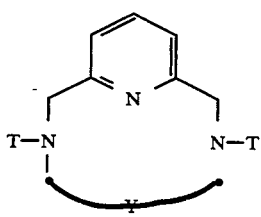

(I)

wherein:
Y is either

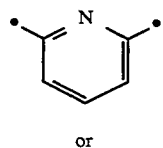

(A)

or

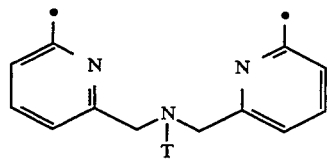

(B)

T is —CH$_2$—COOH, or

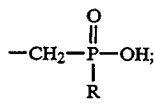

where: R is OH, C$_1$-C$_5$ alkyl or —O—(C$_1$-C$_5$ alkyl); with the proviso that all T moieties are the same or one T is

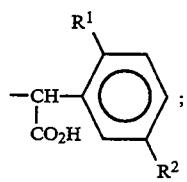

R$^1$ is OH or OCH$_3$;

R$^2$ is NO$_2$, NH$_2$, isothiocyanato, semicarbazido, thiosemicarbazido, maleimido, bromoacetamido or carboxyl; or pharmaceutically-acceptable salts thereof.

When the above ligands of Formula (I) have:

all T equal CH$_2$—P(O)ROH, where R is OH, or the pharmaceutically-acceptable salts thereof, the ligands are referred to herein as BP2P for (A) and TP3P for (B);

all T equal —CH$_2$—COOH, or the pharmaceutically-acceptable salts thereof, the ligands are referred to herein as BP2A (A) and TP3A for (B);

all T equal —CH$_2$—P(O)ROH, where R is —O—(C$_1$-C$_5$ alkyl), or the pharmaceutically-acceptable salts thereof, the ligands are referred to herein as BP2(O-Alk)P for (A) and TP3(O-Alk)P for (B); and all T equal —CH$_2$—P(O)ROH, where R is C$_1$-C$_5$ alkyl, or the pharmaceutically-acceptable salts thereof, the lLigands are referred to herein as BP2(Alk)P for (A) and TP3(Alk)P for (B).

The complexes of this invention can be designed to provide a specific overall charge which advantageously influences the in vivo biolocalization and image contrast. For example, when the metal ion is +3 the following can be obtained:

an overall charge of —3—when Formula (I) is TP3P, which are useful as calcific tissue contrast agents;

an overall charge of —1—when Formula (I) is BP2P, which are useful as calcific tissue contrast agents;

an overall charge of 0—when Formula (I) is TP3A, TP3(O-Alk)P, or TP3(Alk)P, which are useful as general perfusion contrast agents; and an overall charge of +1—when Formula (I) is BP2A, BP2(O-Alk)P, or BP2(Alk)P, which are useful as calcific tissue contrast agents.

The complexes may be formulated to be in a pharmaceutically acceptable form for administration to an animal.

When one T term is other than —CH$_2$—COOH or —CH$_2$—PO$_2$HR, then the compound is a bifunctional ligand/complex and may be linked through R$^2$ to a biologically active molecule.

DETAILED DESCRIPTION OF THE INVENTION

The compounds of Formula (I) are numbered for nomenclature purposes as follows:

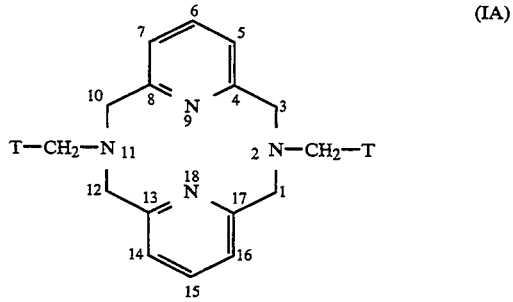

(IA)

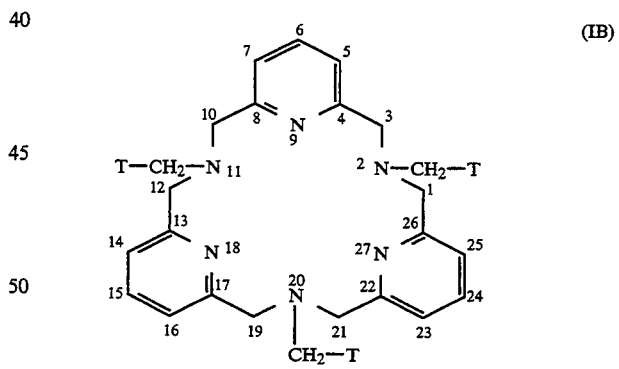

(IB)

One aspect of the present invention concerns development of contrast agents having synthetic modifications to the paramagnetic chelate enabling site specific delivery of the contrast agent to a desired tissue. The advantage being increased contrast in the areas of interest based upon tissue affinity as opposed to contrast arising from non-specific perfusion which may or may not be apparent with an extracellular agent. The specificity of the ligand of Formula (I) may be controlled by adjusting the total charge and lipophilic character of the complex. The overall range of the charge of the complex is from —3 to +1 as indicated above. For example, for a complex having 2 or 3 PO$_3$H$_2$ groups (BP2P and TP3P), the overall charge is highly negative and bone uptake is expected; whereas when the overall charge of the complex is 0 (thus neutral, TP3A, TP3(O-Alk)P, and TP3(Alk)P), the complex may have the ability to cross the blood brain barrier and normal brain uptake may be possible. Unexpectly, for a complex having an overall charge of +1 [BP2A, BP2(O-Alk)P, and BP2(Alk)P], the complex displays bone uptake.

While not wishing to be bound by theory, it is believed that when a charged complex of the invention is made (e.g. possibly −3 for bone, −1 for livery or +1 for heart), the variations in that chelate ionic charge can influence biolocalization.

Tissue specificity may also be realized by ionic or covalent attachment of the chelate to a naturally occurring or synthetic molecule (e.g. through $R^2$) having specificity for a desired target tissue. One possible application of this approach is through the use of chelate conjugated monoclonal antibodies which would transport the paramagnetic chelate to diseased tissue enabling visualization by MRI. In addition, attachment of a paramagnetic chelate to a macromolecule can further increase the contrast agent efficiency resulting in improved contrast relative to the unbound chelate. Recent work by Lauffer (U.S. Pat. Nos. 4,880,008 and 4,899,755) has demonstrated that variations in lipophilicity can result in tissue-specific agents and that increased lipophilic character favors non-covalent interactions with blood proteins resulting in enhancement of relaxivity.

The terms used in Formula (I) and for this invention are further defined as follows. "$C_1$-$C_5$ alkyl", include both straight and branched chain alkyl groups. An "animal" includes a warmblooded mammal, preferably a human being. As used herein, "complex" refers to a complex of the compound of the invention, e.g. Formula (I), complexed with a metal ion, where at least one metal atom is chelated or sequestered.

"Biologically active material" refers to a dextran, peptide, or molecules that have specific affinity for a receptor, or preferably antibodies or antibody fragments.

"Antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "radioactive metal chelate/antibody conjugate" or "conjugate" the "antibody" is meant to include whole antibodies and/or antibody fragments, including semisynthetic or genetically engineered variants thereof. Possible antibodies are 1116-NS-19-9 (anti-colorectal carcinoma), 1116-NS-3d (anti-CEA), 703D4 (anti-human lung cancer), 704A1 (anti-human lung cancer) and B72.3. The hybridoma cell lines 1116-NS-19-9, 1116-NS-3d, 703D4, 704A1, CC49, CC83 and B72.3 are deposited with the American Type Culture Collection, having the accession numbers ATCC HB 8059, ATCC CRL 8019, ATCC HB 8301, ATCC HB 8302, ATCC HB 9459, ATCC HB 9453 and ATCC HB 8108, respectively.

The bifunctional chelating agents described herein (represented by Formula I) can be used to chelate or sequester the metal ions so as to form metal ion chelates (also referred to herein as "complexes"). The complexes, because of the presence of the functionalizing moiety (represented by $R^2$ in Formula I), can be covalently attached to biologically active materials, such as dextran, molecules that have specific affinity for a receptor, or preferably covalently attached to antibodies or antibody fragments. Thus the complexes described herein may be covalently attached to an antibody or antibody fragment or have specific affinity for a receptor and are referred to herein as "conjugates".

As used herein, "pharmaceutically-acceptable salts" means any salt or mixtures of salts of a compound of Formula (I) which is sufficiently non-toxic to be useful in diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic acid, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the compounds of Formula (I) where the salt is potassium, sodium, or ammonium. Also included are mixtures of the above salts.

DETAILED DESCRIPTION OF THE PROCESS

The compounds of Formula (I) are prepared by various processes. Typical general synthetic approaches to such processes are provided by the reaction schemes given below.

In Scheme 1, the compounds of Formula (I) are prepared wherein Y is (A) or (B), and all T moieties are COOH.

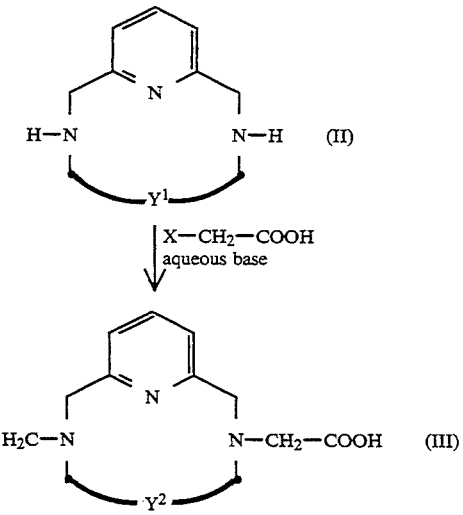

Scheme 1 wherein: $Y^1$ is defined as before for Y when (A) and when (B) the nitrogen atom is substituted with hydrogen; and X is cholro or bromo atom; and $Y^2$ is defined as before for Y when (A) and when (B) the nitrogen atom is substituted with —$CH_2$—COOH.

The aqueous base is alkali metal hydroxide, such as sodium hydroxide or potassium hydroxide. The pH of the reaction is maintained about 8-10. Temperature is between about 60°–90° C., and pressure is not critical so that ambient pressure is used.

In Scheme 2, the compounds of Formula (I) are prepared wherein Y is (A) or (B), and all T moieties are

where: R is OH.

Scheme 2

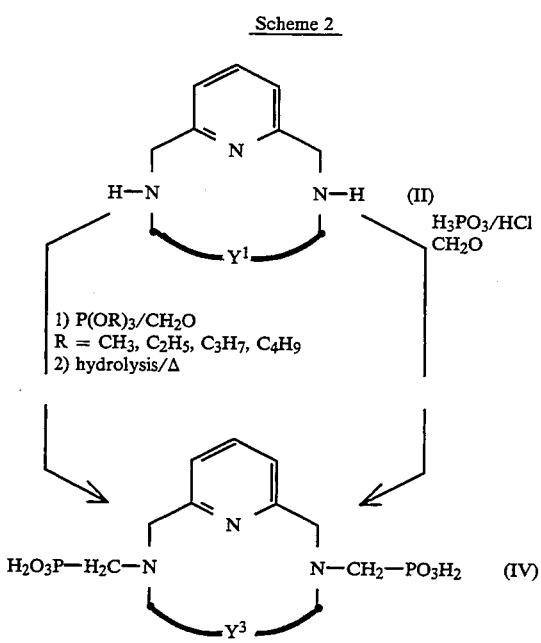

wherein: $Y^1$ is defined as before for Y when (A) and when (B) the nitrogen atom is substituted with hydrogen; $Y^3$ is defined as before for Y when (A) and when (B) the nitrogen atom is substituted with —CH$_2$—PO$_3$H$_2$.

The hydrolysis in Scheme 2 is done by known aqueous acid conditions, such as using 3 to 12M hydrochloric acid. The pH of the reaction is maintained below 3. Temperature is at reflux. Pressure is not critical so that ambient pressure is used. Alternatively, when the reaction is run in one step, phosphorous acid, hydrochloric acid and excess formaldehyde are used. The pH of the reaction is below 2. Temperature is at reflux. Pressure is not critical so that ambient pressure is used.

In Scheme 3, the compounds of Formula (I) are prepared wherein Y is (A) or (B), all T moieties are

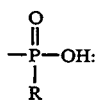

where: R is —O—(C$_1$-C$_5$ alkyl).

Scheme 3

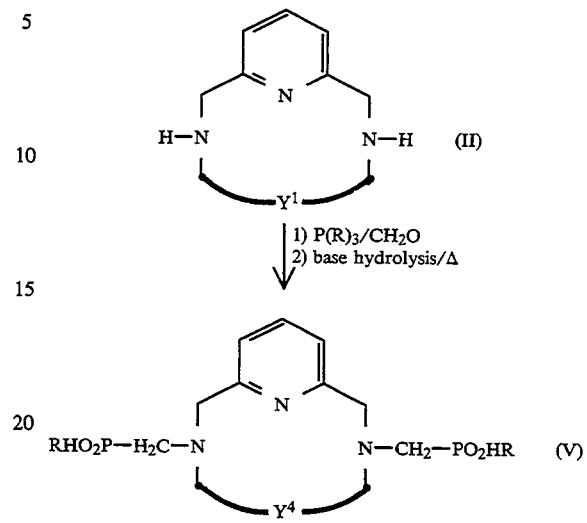

wherein: $Y^1$ is defined as before for Y when (A) and when (B) the nitrogen atom is substituted with hydrogen; $Y^4$ is defined as before for Y when (A) and when (B) the nitrogen atom is substituted with —CH$_2$—PO$_2$HR; and R is —O—(C$_1$-C$_5$ alkyl).

The hydrolysis in Scheme 3 is done under known aqueous basic conditions, such as using excess alkali metal hydroxide, such as sodium or potassium hydroxide. The pH of the reaction is above 9. Temperature is at reflux. Pressure is not critical so that ambient pressure is used.

In Scheme 4, the compounds of Formula (I) are prepared wherein Y is (A) or (B), all T moieties are

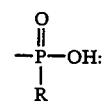

where: R is C$_1$-C$_5$ alkyl.

Scheme 4 shows the preparation of the compounds of Formula (I) when R is methyl.

Scheme 4

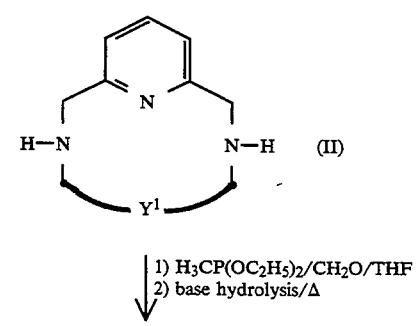

-continued
Scheme 4

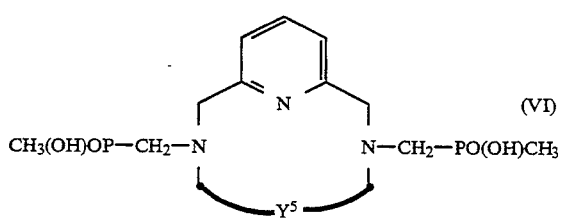
(VI)

wherein: $Y^1$ is defined as before for Y when (A) and when (B) the nitrogen atom is substituted with hydrogen; $Y^5$ is defined as before for Y when (A) and when (B) the nitrogen atom is substituted with —CH$_2$—PO(OH)CH$_3$.

The hydrolysis in Scheme 4 is done under known aqueous basic conditions, such as using excess alkali metal hydroxide, such as sodium or potassium hydroxide. The pH of the reaction is above 9. Temperature is at reflux. Pressure is not critical so that ambient pressure is used.

In Scheme 5, the compounds of Formula (I) are prepared wherein Y is (A) or (B), all T moieties are

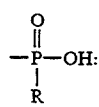

where: R is $C_1$-$C_5$ alkyl.

Scheme 5 shows the preparation of the compounds of Formula (I) when R is ethyl.

Scheme 5

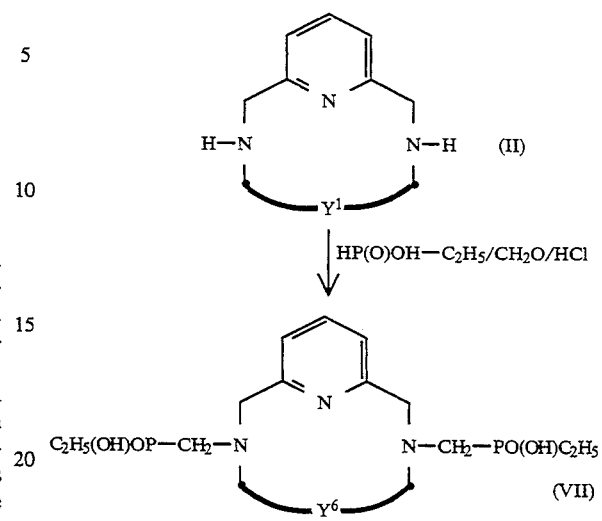

wherein: $Y^1$ is defined as before for Y when (A) and when (B) the nitrogen atom is substituted with hydrogen; $Y^6$ is defined as before for Y when (A) and when (B) the nitrogen atom is substituted with —CH$_2$—PO(OH)C$_2$H$_5$.

The reaction in Scheme 5 is under acidic conditions with a hydrochloric acid. The pH of the reaction is below 3. Temperature is at reflux. Pressure is not critical so that ambient pressure is used.

Scheme 6 shows the preparation of the compounds of Formula (I) when one T is a bifunctional moiety; and the other T is defined above for Formula (I).

Scheme 6

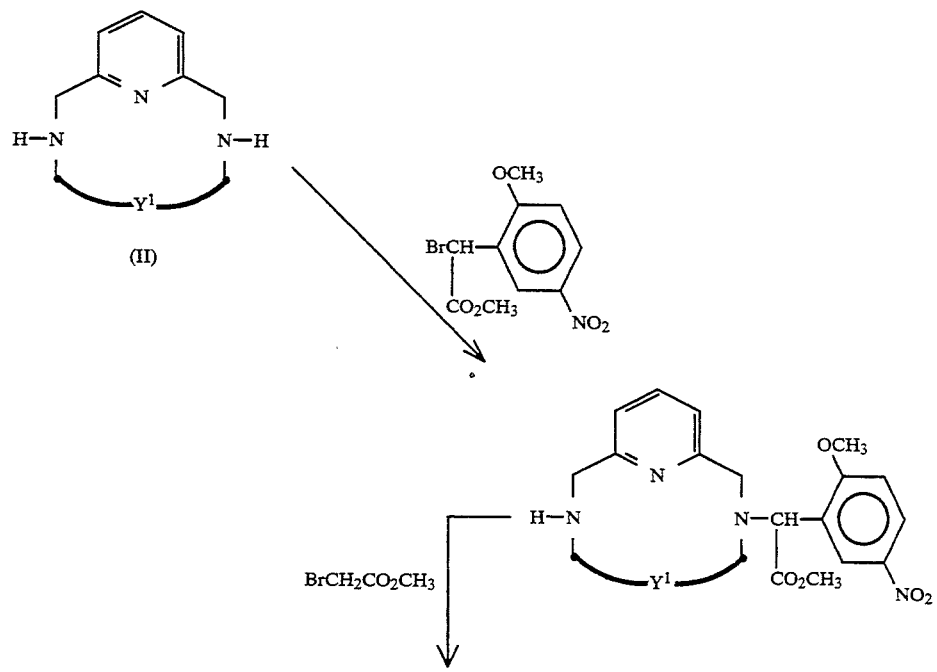

Scheme 6

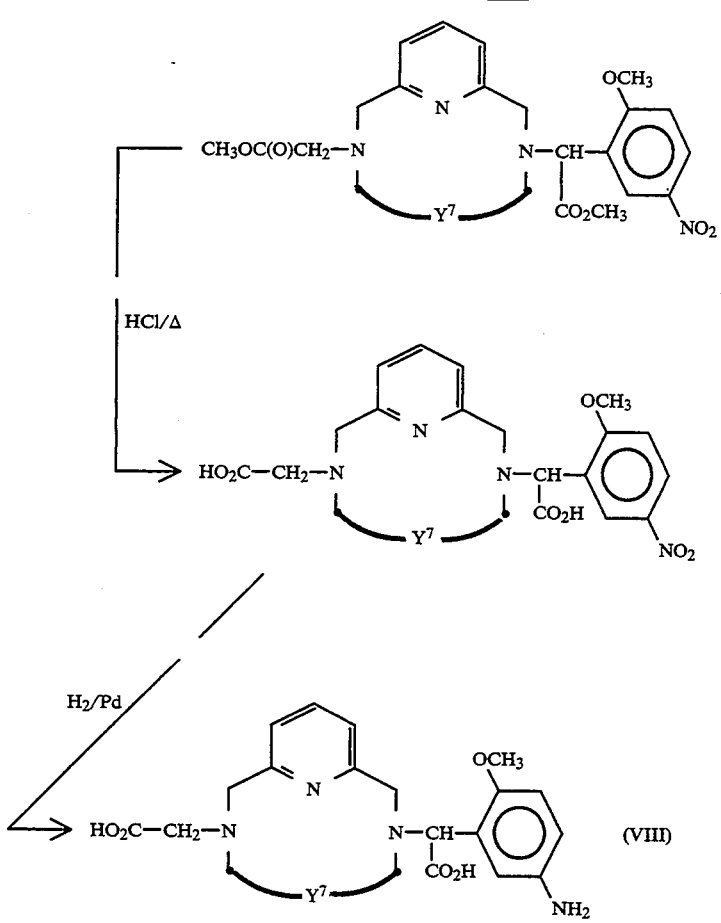

wherein: $Y^1$ is defined as before for Y when (A) and when (B) the nitrogen atom is substituted with hydrogen; $Y^7$ is defined as before for Y when (A) and when (B) the nitrogen atom is substituted with —CH$_2$—CO$_2$H.

In the above Schemes, the general process discription illustrates specific steps that may be used to accomplish a desired reaction step. The general description of these process steps follows.

The general synthetic methodology for preparing 2:2 and 3:3 macrocyclic precursors outlined in Schemes 1–6 is described by Pappalerdo et al., *J. Org. Chem.* 53, 3521–3529 (1988). The carboxylate derivatives described in Scheme 1 are prepared by conventional alkylation procedures utilizing chloro- or bromo-acetic acid under basic aqueous conditions and utilizing the approperiate secondary amine macrocyclic starting material.

The phosphonic acid derivatives outlined in Scheme 2 can be prepared by initial alkylation of the amine with a trialkyl phosphite and paraformaldehyde, resulting in an organic soluble perester. This ester is then hydrolyzed under refluxing acid conditions to give the desired aminophosphonic acids. Alternatively, the phosphonic acid can be prepared under acidic conditions by employing phosphorous acid in combination with formaldehyde and hydrochloric acid.

Phosphonate half esters are prepared as shown in Scheme 3 by initial formation of the dialkyl phosphonate ester, followed by hydrolysis under basic conditions. Base hydrolysis gives exclusive conversion to the half ester.

Scheme 4 illustrates the metholodgy for synthesizing the methyl phosphinate derivatives using diethoxymethylphosphine as the nucleophile and paraformaldehyde. Condensation can be conducted in solvents such as tetrahydrofuran (THF), dimethylformamide (DMF), dioxane, acetonitrile, or alcoholic media. The resulting phosphinate ester is then hydrolyzed under acidic conditions (e.g. 6N HCl, 80°–100° C.) or basic conditions (excess base, 40°–100° C.) to give the corresponding methylphosphonic acid. Alternatively, as outlined in Scheme 5, the method devised by A. D. Sherry et al. (*Inorg. Chem.*, submitted 1991) using ethylphosphonic acid generated in situ can be used to obtain phosphinate derivatives having increased lipophilic character.

Sheme 6 illustrates the preparation of bifunctional compounds of Formula (I) which may then be attached to a biologically active material.

The metal ions used to form the complexes of this invention are $Gd^{+3}$, $Mn^{+2}$, $Fe^{+3}$ and available commercially, e.g. from Aldrich Chemical Company. The anion present is halide, preferrably chloride, or salt free (metal oxide).

A "paramagnetic nuclide" of this invention means a metal ion which displays spin angular momentum and-/or orbital angular momentum. The two types of momentum combine to give the observed paramagnetic moment in a manner that depends largely on the atoms bearing the unpaired electron and, to a lesser extent, upon the environment of such atoms. The paramagnetic nuclides found to be useful in the practice of the invention are gadolinium ($Gd^{+3}$), iron ($Fe^{+3}$) and manganese ($Mn^{+2}$), with $Gd^{+3}$ being preferred.

The complexes are prepared by methods well known in the art. Thus, for example, see Chelating Agents and Metal Chelates, Dwyer & Mellor, Academic Press (1964), Chapter 7. See also methods for making amino acids in *Synthetic Production and Utilization of Amino Acids*, (edited by Kameko, et al.) John Wiley & Sons (1974). An example of the preparation of a complex involves reacting a bicyclopolyazamacrocyclophosphonic acid with the metal ion under aqueous conditions at a pH from 5 to 7. The complex formed is by a chemical bond and results in a stable paramagnetic nuclide composition, e.g. stable to the disassociation of the paramagnetic nuclide from the ligand.

The complexes of the present invention are administered at a ligand to metal molar ratio of at least about 1:1, preferably from 1:1 to 3:1, more preferably from 1:1 to 1.5:1. A large excess of ligand is undesirable since uncomplexed ligand may be toxic to the animal or may result in cardiac arrest or hypocalcemic convulsions.

This invention is used with a physiologically acceptable carrier, excipient or vehicle therefore. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis. The dose will vary depending on the disease and physical parameters of the animal, such as weight. In vivo diagnostics are also contemplated using formulations of this invention.

Other uses of some of the chelants of the present invention may include the removal of undesirable metals (i.e. iron) from the body, attachment to polymeric supports for various purposes, e.g. as diagnostic agents, and removal of metal ions by selective extraction. The ligands of Formula (I) having in at least two R terms T equal to $P(O)R^1OH$ may be used for metal ion control as scale inhibitors. Some of these ligands can be used in less than stoichiometric amounts. Similar uses are known for compounds described in U.S. Pat. Nos. 2,609,390; 3,331,773; 3,336,221; and 3,434,969.

The invention will be further clarified by a consideration of the following examples, which are intended to be purely exemplary of the present invention.

Some terms used in the following examples are defined as follows:
LC = liquid chromatrography, purifications were carried out at low pressure using Dionex 2010i system fitted with a hand-packed Q-Sepharose TM anion exchange column (23×2 cm).
DMF = dimethylforamide.
AcOH = acetic acid.
g = gram(s).
mg = milligrams.
kg = kilogram(s).
mL = milliliter(s).
$\mu L$ = microliter(s).

pH Stability General Procedure

A stock $^{159}GdCl_3$ (or $^{153}SMCl_3$) solution was prepared by adding 2 $\mu L$ of $3\times10^{-4}M$ $^{159}GdCl_3$ in 0.1N HCl to 2 mL of a $3\times10^{-4}M$ $GdCl_3$ carrier solution. Appropriate ligand solutions were then prepared in deionized water. The 1:1 ligand/metal complexes were then prepared by combining the ligands (dissolved in 100–500 $\mu L$ of deionized water) with 2 mL of the stock $^{159}GdCl_3$ solution, followed by through mixing to give an acidic solution (pH=2). The pH of the solution was then raised to 7.0 using 0.1N NaOH. The percent metal as a complex was then determined by passing a sample of the complex solution through a Sephadex TM G-50 column, eluting with 4:1 saline (85% $NaCl/NH_4OH$) and collecting 2×3 mL fractions. The amount of radioactivity in the combined elutions was then compared with that left on the resin (non-complexed metal is retained on the resin). The pH stability profile was generated by adjusting the pH of an aliquot of the complex solution using 1M NaOH or 1M HCl and determining the percent of the metal existing as a complex using the ion exchange method described above. The Sm results are known by experimntal comparison to be identical for complexation and biodistribution of the ligands of this invention.

SYNTHESIS OF LIGANDS.

General Materials and Methods.

All reagents were obtained from commercial suppliers and used as received without further purification. NMR spectra were recorded on a Bruker AC-250 MHz spectrometer equipped with a multi-nuclear quad probe ($^1H$, $^{13}C$, $^{31}P$, and $^{19}F$) at 297° K. unless otherwise indicated. $^1H$ spectra in $D_2O$ were recorded by employing solvent suppression pulse sequence ("PRESAT", homo-nuclear presaturation). $^1H$ spectra are referenced to residual chloroform (in $CDCl_3$) at $\delta 7.26$ or external dioxane (in $D_2O$) at $\delta 3.55$. $^{13}C$ and $^{31}P$ spectra reported are proton decoupled (broad band). Assignments of $^{13}C$ {$^1H$} chemical shifts were aided by DEPT (Distortionless Enhancement by Polarization Transfer) experiments. $^{13}C$ {$^1H$} spectra are referenced to center peak of $CDCl_3$ at $\delta 77.00$ (in $CDCl_3$) and external dioxane at $\delta 66.66$ (in $D_2O$). $^{31}P$ {$^1H$} spectra were referenced to external 85% $H_3PO_4$ at $\delta 0.00$. Melting points Were determined by capilliary melt methods and were uncorrected. Semipreparative ion-exchange chromatographic separations were performed at low pressure (<600 psi) using a 5 standard glass column fitted with hand-packed Q-Sepharose TM (anion exchange) or SP-Sepharose TM (cation exchange) glass column, and with on-line UV detector at 263 nm for eluent monitoring. GC/MS spectra were performed on a Hewlett Packard 5890A Gas Chromatograph/5970 Mass Selective Detector.

STARTING MATERIALS

EXAMPLE A

Preparation of N,N'-ditosyl-2,11-diaza[3.3]-(2,6)pyridinophane.

To a stirred solution of tosylamide, sodium salt (TsNHNa), (13.52 g, 70 mmol) in anhydrous DMF (1.3 L) at 80° C. was added dropwise (1.5 hr) under a $N_2$ atmosphere a solution of 2,6-bis(chloromethyl)pyridine (12.32 g, 70 mmol) in DMF (200 mL). After 1 hr, solid TsNHNa (13.52 g, 70 mmol) was added all at once, and the mixture was stirred at 80° C. for additional 16 hr. The reaction mixture was then cooled to room temperature and decanted. The solvent was removed in vacuo and the resulting residue was combined with acetone and filtered to give a waxy solid which was continuously extracted (Soxlet) with acetone (300 mL) for 48 hr. The product was isolated as the precipitate at the bottom of the heating flask. Upon drying, the product was isolated as white powder (5.24 g, 27%): mp=246°-248° C. and further characterized by:
$^1$H NMR (DMSO-d 6)
δ 2.42 (s, 6H), 4.38 (s, 8H), 6.99 (d, 4H), 7.40–7.49 (m, 6H), 7.88 (d, 4H); and
$^{13}$C {$^1$H} NMR (DMSO-d6)
δ 20.91, 55.55, 122.12, 126.92, 129.88, 135.99, 137.03, 143.30, 154.71; and is illustrated by the formula

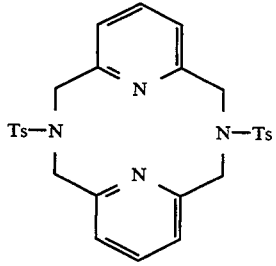

EXAMPLE B

Preparation of 2,11-diaza[3.3](2,6)pyridinophane.

N,N'-ditosyl-2,11-diaza[3.3](2,6)pyridinophane (5.24 g, 9.5 mmol), prepared in Example A, was dissolved in 90% H$_2$SO$_4$ (48 mL) and heated at 110° C. with stirring for 2 hr. After the solution was cooled to room temperature, it was slowly diluted with deionized water (50 mL) while chilling in an ice bath. The resulting solution was then poured into a 25% NaOH solution (200 mL) which was cooled in an ice bath. The resulting white solid was extracted with CHCl$_3$ (3×100 mL), dried over anhydrous MgSO$_4$, filtered, and concentrated to dryness to give the titled product as a waxy white solid (1.69 g, 74%) and further characterized by:
$^1$H NMR (CDCl$_3$)
δ 3.91 (s, 8 H), 6.47 (d, 4H), 7.06 (t, 2H); and
$^{13}$C {$^1$H} NMR (CDCl$_3$)
δ 55.89, 119.73, 135.71, 159.36:
CG/mass spectra m/z M+240; and is illustrated by the formula

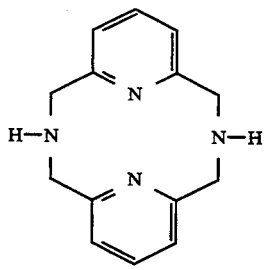

EXAMPLE C

Preparation of N,N',N''-tritosyl-2,11,20-triaza[3.3.3](2,6)pyridinophane.

Isolated as a by-product from the reaction used for preparation of N,N'-ditosyl-2,11-diaza[3.3](2,6-)pyridinophane, prepared in Example A, (remaining part on the extractor thimble after Soxlet extraction) mp 260°-262° C.; and further characterized by:
$^1$H NMR (DMSO-d6)
δ 2.31 (s, 9H), 4.08 (s, 12H), 7.01 (d, 4H), 7.30 (d, 6H), 7.52 (t, 3H), 7.67 (d, 6H); and $^{13}$C {$^1$H} NMR (DMSO-d6)
δ 20.92, 54.03, 120.55, 127.13, 129.83, 135.12, 136.83, 143.45, 155.47; and is illustrated by the formula:

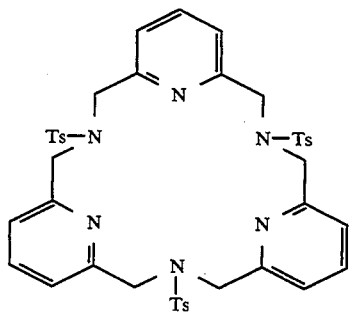

EXAMPLE D

Preparation of 2,11,20-triaza[3.3.3](2,6)pyridinophane.

N,N',N''-tritosyl-2,11,20-triaza[3.3.3]-(2,6)pyridinophane (0.5 g, 0.61 mmol), prepared in Example C was dissolved in 90% H$_2$SO$_4$ (6 mL) and heated at 110° C. with stirring for 2 hr. The solution was then cooled to room temperature and slowly diluted with deionized water (6 mL) while chilling in a ice bath. The resulting solution was then poured into a 25% NaOH solution (22 ml) which was cold in an ice bath. The resulting white solid was extracted with CHCl$_3$ (2×30 mL), dried over anhydrous MgSO$_4$, filtered, and concentrated in vacuo to dryness to give the titled product as a waxy white solid (0.167 g, 76%); and further characterized by:
$^1$H NMR (CDCl$_3$)
δ 3.03 (s, 3H), 3.93 (s, 12H), 7.08 (d, 6H), 7.54 (t, 3H); and
$^{13}$C {$^1$H} NMR (CDCl$_3$)
δ 54.58, 120.72, 136.50, 158.64;
GC/mass spectra m/z M+360; and is illustrated by the formula:

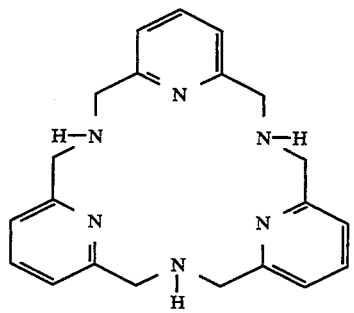

EXAMPLE E

Preparation of N,N'-bis(methylenedimethylphosphonate)-2,11-diaza[3.3](2,6)pyridinophane.

The product prepared in Example B, 2,11-diaza[3.3](2,6)pyridinophane (276.4 mg, 1.15 mmol) was combined with paraformaldehyde (138 mg, 4.60 nunol, excess) and trimethylphosphite (0.814 mL, 855 mg, 4.60 mmol, excess). After the mixture was gently stirred for 10 min to obtain a well mixed slurry, it was heated to 85° C. and maintained for 1 hr. After the excess reagents and byproducts were removed in vacuo (1 hr at 110° C./0.01 mmHg), the dark brown residue was dissolved in CHCl₃ (20 mL) and washed with deionized water (5×15 mL). The organic layer was dried over anhydrous MgSO₄, filtered, and the solvent was removed in vacuo to give the product as a yellow waxy solid (363 mg, 65%); and further characterized by:

¹H NMR (CDCl₃)

δ 3.39 (d, 4H), 3.88 (d, 12H), 4.08 (s, 8H), 6.84 (d, 4H), 7.13 (t, 2H); and

¹³C {¹H} NMR (CDCl₃)

δ 52.75 (d), 54.88 (d), 65.21 (d), 122.71, 135.69, 157.14; and

³¹P NMR (CDCl₃)

δ 27.22; and is illustrated by the formula

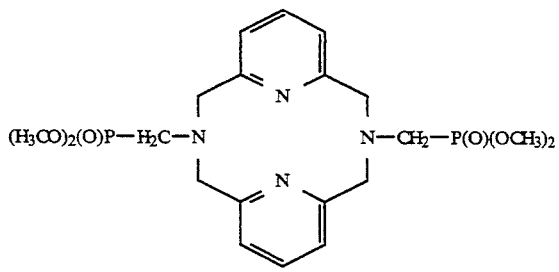

EXAMPLE F

Preparation of N,N'-bis(methylenediethylphosphonate)-2,11-diaza[3.3](2,6)pyridinophane.

The product prepared in Example B, 2,11diaza-[3.3](2,6)pyridinophane (0.47 g, 1.96 mmol) was combined with paraformaldehyde (235 mg, 7.84 mmol, excess) and triethylphosphite (1.34 mL, 1.30 g, 7.84 mmol, excess). After the mixture was gently stirred for 10 min to obtain a well niixed slurry, it was heated to 90° C. for 1 hr. After the excess reagents and byproducts were removed in vacuo (1 hr at 125° C./0.01 mmHg), the resulting dark brown residue was dissolved in CHCl₃ (20 mL) and washed with deionized water (5×15 mL). The organic layer was dried over anhydrous MgSO₄, filtered, and the solvent was removed in vacuo to give the product as a yellow waxy solid (957 mg, 91%); and further characterized by:

¹H NMR (CDCl₃)

δ 1.24 (t, 12H), 3.20 (d, 4H), 3.94 (s, 8H), 4.07 (q, 8H), 6.71 (d, 4H), 6.98 (t, 2H); and ¹³C {¹H} NMR (CDCl3)

δ 16.48, 55.36 (d), 61.75 (d), 65.14 (d), 122.52, 135.41, 157.04; and

³¹P {¹H} NMR (CDCl₃)

δ 24.60; and is illustrated by the formula

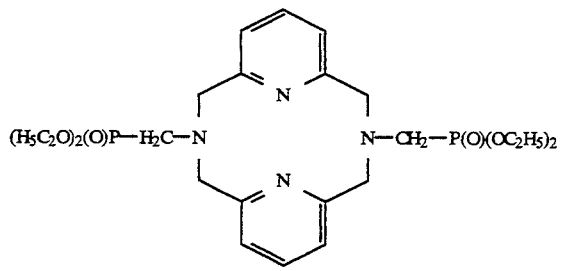

FINAL PRODUCTS

Ligands: Preparation of tri- and dimethylenecarboxylic acids as shown in Scheme 1.

EXAMPLE 1

Preparation of N,N'-diacetic acid-2,11-diaza[3.3]-(2,6)pyridinophane (BP2A).

To a stirred aqueous solution (1 mL) of 2,11-diaza[3.3](2,6)pyridinophane, prepared in Example B, (82.4 mg, 0.58 mmol) was added bromoacetic acid (275 mg, 1.98 mmol, excess) and the pH of the reaction mixture was maintained above 10 by adding small portions of conc. NaOH until no more caustic was needed to keep pH>11 (~30 min). The reaction mixture was then heated (60° C.) for 2 hr, then the reaction mixture was cooled to room temperature, the pH of the reaction mixture adjusted to 7. The solution was then chromatographed on cation exchange (SP-Sepharose ™) column (1.5×50 cm) eluting first with deionized water then with 1M HCl. The acidic fraction containing product was evaporated to dryness, followed by coevaporation with fresh deionized water (3×2 mL) to eliminate excess HCl. The final product was isolated as a white solid upon freeze drying of the concentrated aqueous solution from above; and characterized by:

¹H NMR (D₂O)

δ 4.17 (s, 4H), 4.43 (s, 8H), 7.15 (d, 4H), 7.66 (t, 2H); and

¹²C {¹H} NMR (D₂O)

δ 61.44, 61.70, 127.46, 146.84, 154.37, 175.62.

EXAMPLE 2

Preparation of N,N',N''-triacetic acid-2,11,20-diaza[3.3.3](2,6)pyridinophane (TP3A).

To a stirred aqueous solution (1 mL) of 2,11,20-triaza[3.3.3](2,6)pyridinophane, prepared in Example D, (54.5 mg, 0.15 mmol) was added bromoacetic acid (100 mg, 0.72 mmol, excess) and the pH of the reaction mixture was maintained above 10 by adding small portions of conc. NaOH until no more caustic was needed to keep the final pH>11 (~30 min). The reaction mixture was then heated (60° C.) for 2 hr, cooled to room temperature, and pH adjusted to 7. The aqueous solution was then chromatographed on a cation exchange (SP-Sepharose ™) colunm (1.5×50 cm) eluting first with deionized water then with 1M HCl. The acidic fraction containing product was evaporated to dryness, followed by coevaporation with fresh deionized water (3×2 mL) to eliminate excess HCl. The final product was isolated as white solid upon freeze drying of the concentrated aqueous solution from above; and characterized by:

¹H NMR (D₂O)

δ 4.12 (s, 6H), 4.68 (s, 12H), 7.41 (d, 6H), 7.81 (t, 3H); and

¹³C {¹H} NMR (D₂O)

δ 57.32, 60.53, 128.57,143.42,152.42,171.17.

Ligands: Preparation of dimethylenephosphonic acids as shown in Scheme 2.

EXAMPLE 3

Preparation of N,N'-bis (methylenephosphonic acid) -2,11-diaza[3.3](2,6)pyridinophane (BP2P).

A conc. HCl solution (37%,4 mL) of N,N'-bis(methylenedimethylphosphonate)-2,11-diaza[3.3]-(2,6) pyridinophane, prepared in Example E, (255 mg, 0.53 mmol) was heated at reflux for 2.5 hr. After cooling, the solution was evaporated to dryness, followed by coevaporation with fresh deionized water (3×2 mL) to eliminate excess HCl. The final product was isolated as a hygroscopic brown solid upon freeze-drying of the concentrated aqueous solution; and characterized by:

$^1$H NMR (D$_2$O)
δ 3.55 (d, 4H), 4.46 (br s, 8H), 6.90 (d, 4H), 7.37 (t, 2H); and $^{13}$C {$^1$H} NMR (D$_2$O)
δ 57.80 (d), 63.74 (d), 127.02, 144.18, 152.96; and $^{31}$P {$^1$H} NMR (D$_2$O)
δ 11.71.

Ligands: Preparation of dimethylenephosphonate half esters as shown in Scheme 3.

EXAMPLE 4

Preparation of N,N'-bis(methylenephosphonic acid ethyl ester)-2,11-diaza[3.3](2,6)pyridinophane (BP2EP).

The product prepared in Example F, N,N'-bis(methylenediethylphosphonate)-2,11-diaza[3.3](2,6-)pyridinophane, (957 mg, 1.77 mmol) was combined with 0.1M KOH (7.2 mL) and heated at 60° C. for 16 hr. The solution was then cooled and freeze-dried to give a residue which was dissolved into CHCl$_3$/C$_2$H$_5$OH (95/5), and filtered. Upon evaporation of solvent and concentration in vacuo, the product was isolated as a pale yellow powder (657 mg, 66%); and characterized by:

$^1$H NMR (D$_2$O)
δ 1.10 (t, 6H), 2.97 (d, 4H), 3.81 (q, 4H), 3.84 (s, 8H), 6.73 (d, 4H), 7.09 (t, 2H); and $^{13}$C {$^1$H} NMR (D$_2$O)
δ 18.98, 58.76 (d), 63.69 (d), 66.53 (d), 126.35, 140.09,159.37; and $^{31}$P {$^1$H} NMR (D$_2$O)
δ 20.65.

Complexes: Preparation of metal/ligand complexes for biodistribution studies.

General Procedure

Metal ligand complexes were prepared by various methods. The methods included mixing of the metal and ligand in aqueous solution and adjusting the pH to the desired value. Complexation was done in solutions containing salts and/or buffers as well as water. Sometimes heated solutions were found to give higher complex yields than when the complexation was done at ambient temperatures.

For example, a solution of the ligand is prepared by dissolving the ligand in deionized water (about pH=2). A ligand/metal complex was then prepared by combining the ligand solution with aqueous SmCl$_3$.H$_2$O (3×$^{-4}$M in 0.01N HCl) containing tracer $^{153}$SmCl$_3$. After thorough mixing, the percent metal as a complex was determined by passing a sample of the complex solution through a Sephadex TM column, eluting with 4:1 saline (0.85% NaCl/NH$_4$OH), and collecting 2×3 mL fractions. The amount of radioactivity in the combined elutions was then compared with that left on the resin. Under these conditions, complex was removed with the eluent and non-complexed metal is retained on the resin. By this method complexation was determined to usually be about 95% or greater.

Using the above procedure, the complexes of samarium with

N,N'-diacetic acid-2,11-diaza[3.3]-(2,6)pyridinophane (BP2A), ligand:metal ratio of 4:1, 99%;

N,N',N''-triacetic acid-2,11,20-diaza[3.3.3](2,6-)pyridinophane (TP3A), ligand:metal ratio of 3:1, 98.6%;

N,N'-bis(methylenephosphonic acid)-2,11-diaza[3.3](2,6)pyridinophane (BP2P), ligand:metal ratio of 3:1, 95%; and N,N'-bis(methylenephosphonic acid ethyl ester)-2,11-diaza[3.3](2,6)pyridinophane (BP2EP), ligand:metal ratio of 4:1, 98%;

were made. However, in an anologous manner the corresponding galdolinium complexes may be prepared.

BIODISTRIBUTION

General Procedure

Sprague Dawley rats were allowed to acclimate for five days then injected with 100 μL of the complex solution via a tail vein. The rats weighed between 150 and 250 g at the time of injection. After 30 min. the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ.

The percent dose in blood was estimated assuming blood to be 6.5% of the total body weight. The percent dose in bone was estimated by multiplying the percent dose in the femur by 25. The percent dose in muscle was estimated assuming muscle to be 43% of the total body weight.

In addition to organ biodistribution, chelates of the compounds of Formula (I) were evaluated for efficiency of bone localization since phosphonates are known for their ability to bind to hydroxyapatite. The results of these tests are given below.

EXAMPLE I

When the complex $^{153}$Sm ∎ N,N'-diacetic acid-2,11-diaza[3.3](2,6)pyridinophane] ($^{153}$Sm-BP2A) was evaluated, the results are given in Table I below. The numbers represent the average of a minimum of 2 rats per data point at 2 hours post injection.

TABLE I

| BIODISTRIBUTION OF $^{153}$Sm-BP2A % INJECTED DOSE | |
|---|---|
| ORGAN | AVERAGE |
| Bone | 27.98 |
| Liver | 0.68 |
| Kidney | 0.95 |
| Spleen | 0.01 |
| Muscle | 0.80 |
| Blood | 0.43 |
| Heart | 0.02 |
| Lung | 0.06 |
| Brain | 0.01 |
| Stomach | 0.05 |
| Small Intestine | 0.80 |
| Large Intestine | 0.04 |

TABLE I

| RATIOS FOR $^{153}$Sm-BP2A AVERAGE % INJECTED DOSE FOR $^{159}$Gd-BP2EP | | | |
|---|---|---|---|
| Bone/Blood | Bone/Muscle | Bone/Liver | Bone/Spleen |
| 65 | 35 | 41 | 2,798 |

EXAMPLE II

When the complex $^{153}$Sm N,N',N''-triacetic acid-2,11,20-diaza[3.3.3](2,6)pyridinophane] ($^{153}$Sm-TP3A) was evaluated, the results are given in Table II below. The numbers represent 1 rat per data point at 2 hours post injection.

TABLE II

BIODISTRIBUTION OF $^{153}$Sm-TP3A
% INJECTED DOSE

| ORGAN | % INJECTED DOSE |
|---|---|
| Bone | 1.495 |
| Liver | 0.570 |
| Kidney | 0.639 |
| Spleen | 0.068 |
| Muscle | 0.833 |
| Blood | 0.437 |
| Heart | 0.016 |
| Lung | 0.047 |
| Stomach | 0.036 |
| Small Intestine | 1.426 |
| Large Intestine | 0.156 |

TABLE II

RATIOS FOR $^{153}$Sm-TP3A
AVERAGE % INJECTED DOSE

| Bone/Blood | Bone/Muscle | Bone/Liver | Bone/Spleen |
|---|---|---|---|
| 3 | 2 | 3 | 22 |

EXAMPLE III

When the complex $^{153}$Sm ∎ N,N'-bis(methylenephosphonic acid)-2,11-diaza[3.3](2,6)pyridinophane] ($^{153}$Sm-BP2P) was evaluated, the results are given in Table III below. The numbers represent 3 rats per data point at 2 hours post injection.

TABLE III

BIODISTRIBUTION OF $^{153}$Sm-BP2P
% INJECTED DOSE

| ORGAN | AVERAGE |
|---|---|
| Bone | 60.08 |
| Liver | 3.71 |
| Kidney | 1.21 |
| Spleen | 0.05 |
| Muscle | 1.53 |
| Blood | 0.87 |
| Heart | 0.07 |
| Lung | 0.17 |
| Brain | 0.01 |
| Stomach | 0.20 |
| Small Intestine | 0.39 |
| Large Intestine | 0.13 |

TABLE III

RATIOS FOR $^{153}$Sm-BP2P
AVERAGE % INJECTED DOSE

| Bone/Blood | Bone/Muscle | Bone/Liver | Bone/Spleen |
|---|---|---|---|
| 69 | 39 | 16 | 1,201 |

EXAMPLE IV

When the complex $^{53}$Sm ∎ N,N'-bis(methylenephosphonic acid ethyl ester)-2,11-diaza[3.3](2,6)pyridinophane] ($^{153}$Sm-Bp2EP) was evaluated, the results are given in Table IV below. The numbers represent 3 rats per data point at 2 hours post injection.

TABLE IV

BIODISTRIBUTION OF $^{153}$Sm-BP2EP
% INJECTED DOSE

| ORGAN | AVERAGE |
|---|---|
| Bone | 39.82 |
| Liver | 5.97 |
| Kidney | 0.74 |
| Spleen | 0.32 |
| Muscle | 1.21 |
| Blood | 0.45 |
| Heart | 0.04 |
| Lung | 0.19 |
| Brain | 0.01 |
| Stomach | 0.36 |
| Small Intestine | 0.33 |
| Large Intestine | 0.25 |

TABLE IV

RATIOS FOR $^{153}$Sm-BP2E
AVERAGE % INJECTED DOSE

| Bone/Blood | Bone/Muscle | Bone/Liver | Bone/Spleen |
|---|---|---|---|
| 88 | 33 | 7 | 124 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. Tri- and tetra-cyclopolyazamacrocyclic compounds of the formula

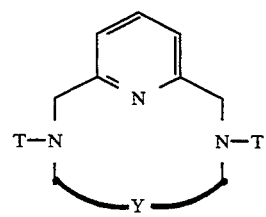

(I)

wherein:
Y is either

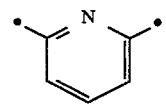

(A)

or

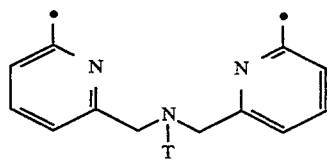

(B)

T is —CH$_2$—COOH or

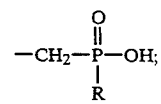

where: R is OH, $C_1$-$C_5$ alkyl or —O—($C_1$-$C_5$ alkyl); with the proviso that all T moieties are the same or one T moiety is

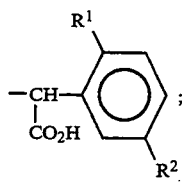

$R^1$ is OH or $OCH_3$;

$R^2$ is $NO_2$, $NH_2$, isothiocyanato, semicarbazido, thiosemicarbazido, maleimido, bromoacetamido or carboxyl; or pharmaceutically-acceptable salts thereof.

2. A compound of claim 1 wherein all T moieties are equal to —$CH_2$—P(O)ROH, where R is OH.

3. A compound of claim 2 wherein the compound is a compound of Formula (IA) which has two T moieties equal to —$CH_2$—P(O)ROH, where R is OH, or pharmaceutically-acceptable salts thereof, and which compound is named N,N'-bis(methylenephosphonic acid)-2,11-diaza[3.3](2,6)pyridinophane.

4. A compound of claim 1 wherein all T equal —$CH_2$—COOH.

5. A compound of claim 4 wherein the compound is a compound of Formula (IA) which has two T moieties equal to —$CH_2$—COOH, or pharmaceutically-acceptable salts thereof, and which compound is named N,N'-diacetic acid-2,11-diaza[3.3](2,6)pyridinophane.

6. A compound of claim 4 wherein the compound is a compound of Formula (IB) which has three T moieties equal to —$CH_2$—COOH, or pharmaceutically-acceptable salts thereof, and which compound is named N,N',N''-triacetic acid-2,11,20-diaza[3.3.3](2,6-)pyridinophane.

7. A compound of claim 1 wherein all T equal —$CH_2$—P(O)ROH, where R is —O—($C_1$-$C_5$ alkyl).

8. A compound of claim 7 wherein the compound is a compound of Formula (IA) which has two T moieties equal to —$CH_2$—P(O)ROH, where R is —O—($C_1$-$C_5$ alkyl), or pharmaceutically-acceptable salts thereof.

9. A compound of claim 8 wherein R is ethoxy, or pharmaceutically-acceptable salts thereof, and the compound is named N,N'-bis(methylenephosphonic acid ethyl ester)-2,11-diaza[3.3](2,6)pyridinophane.

10. A compound of claim 1 wherein all T equal —$CH_2$—P(O)ROH, where R is $C_1$-$C_5$ alkyl.

11. A compound of claim 1 where one T is

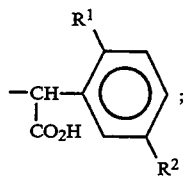

where $R^1$ and $R^2$ are defined as in claim 1; and all the other T terms are —$CH_2$—COOH.

12. A complex which comprises a tri- and tetra-cyclopolyazamacrocyclic compound of the formula

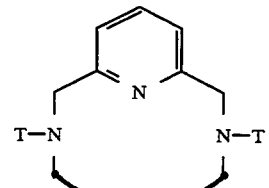

wherein:
Y is either

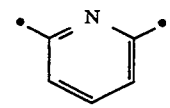

or

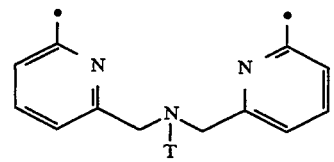

T is —$CH_2$—COOH or

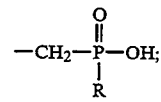

where: R is OH, $C_1$-$C_5$ alkyl or —O—($C_1$-$C_5$ alkyl); with the proviso that all T moieties are the same: or one T moiety is

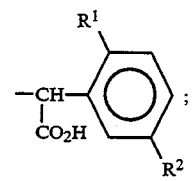

$R^1$ is OH or $OCH_3$;

$R^2$ is $NO_2$, $NH_2$, isothiocyanato, semicarbazido, thiosemicarbazido, maleimido, bromoacetamido or carboxyl; or pharmaceutically-acceptable salts thereof;

complexed with a metal ion selected from $Gd^{+3}$, $Mn^{+2}$ or $Fe^{+3}$.

13. A complex of claim 12 wherein the metal is $Gd^{+3}$.

14. A complex of claim 12 wherein all T moieties are equal to —$CH_2$—P(O)ROH, where R is OH, and the metal is $Gd^{+3}$.

15. A complex of claim 14 wherein the compound is a compound of Formula (IA) which has two T moieties equal to —$CH_2$—P(O)ROH, where R is OH, or pharmaceutically-acceptable salts thereof, and which compound is named N,N'-bis(methylenephosphonic acid)-2,11-diaza[3.3](2,6)pyridinophane.

16. A complex of claim 12 wherein all T equal —$CH_2$—COOH, and the metal is $Gd^{+3}$.

17. A complex of claim 16 wherein the compound is a compound of Formula (IA) which has two T moieties equal to —CH$_2$—COOH, or pharmaceutically-acceptable salts thereof, and which compound is named N,N'-diacetic acid-2,11-diaza[3.3](2,6)pyridinophane.

18. A complex of claim 16 wherein the compound is a compound of Formula (IB) which has three T moieties equal to —CH$_2$—COOH, or pharmaceutically-acceptable salts thereof, and which compound is named N,N',N''-triacetic acid-2,11,20-diaza[3.3.3](2,6-)pyridinophane.

19. A complex of claim 12 wherein all T equal —CH$_2$—P(O)ROH, where R is —O—(C$_1$-C$_5$ alkyl), and the metal is Gd$^{+3}$.

20. A complex of claim 19 wherein the compound is a compound of Formula (IA) which has two T moieties equal to —CH$_2$—P(O)ROH, where R is —O—(C$_1$-C$_5$ alkyl), or pharmaceutically-acceptable salts thereof.

21. A complex of claim 20 wherein R is ethoxy, or pharmaceutically-acceptable salts thereof, and the compound is named N,N'-bis(methylenephosphonic acid ethyl ester)-2,11-diaza[3.3](2,6)pyridinophane.

22. A complex of claim 12 wherein all T equal —CH$_2$—P(O)ROH, where R is C$_1$-C$_5$ alkyl, and the metal is Gd$^{+3}$.

23. A pharmaceutical formulation comprising a complex of claim 12 with a pharmaceutically-acceptable carrier.

24. A pharmaceutical formulation comprising a complex of claim 14 with a pharmaceutically-acceptable carrier.

25. A pharmaceutical formulation comprising a complex of claim 16 with a pharmaceutically-acceptable carrier.

26. A pharmaceutical formulation comprising a complex of claim 19 with a pharmaceutically-acceptable carrier.

27. A pharmaceutical formulation comprising a complex of claim 22 with a pharmaceutically-acceptable carrier.

* * * * *